(12) United States Patent
Omori

(10) Patent No.: US 6,433,173 B1
(45) Date of Patent: Aug. 13, 2002

(54) PROCESS FOR THE PREPARATION OF IPIDACRINE OR IPIDACRINE HYDROCHLORIDE HYDRATE

(75) Inventor: Hiromasa Omori, Saitama (JP)

(73) Assignee: Nikken Chemicals Co., Ltd., Tokyo (JP)

( * ) Notice: Subject to any disclaimer, the term of this patent is extended or adjusted under 35 U.S.C. 154(b) by 0 days.

(21) Appl. No.: 10/019,986

(22) PCT Filed: Jul. 6, 2000

(86) PCT No.: PCT/JP00/04525

§ 371 (c)(1),
(2), (4) Date: Jan. 4, 2002

(87) PCT Pub. No.: WO01/04094

PCT Pub. Date: Jan. 18, 2001

(30) Foreign Application Priority Data

Jul. 9, 1999 (JP) ............................................. 11-195430

(51) Int. Cl.$^7$ ...................... C07D 22/16; A61K 31/473
(52) U.S. Cl. ........................................ 546/79; 514/290
(58) Field of Search ............................ 546/79; 514/290

(56) References Cited

U.S. PATENT DOCUMENTS 4,550,113 A   10/1985   Lavretskaya et al. ....... 514/290

FOREIGN PATENT DOCUMENTS

JP   63-297367   12/1988

*Primary Examiner*—Charanjit S. Aulakh
(74) *Attorney, Agent, or Firm*—Christie, Parker & Hale, LLP

(57) ABSTRACT

A process for the preparation of ipidacrine (I) (9-amino-2,3,5,6,7,8-hexahydro-1H-cyclopenta[b]quinoline)

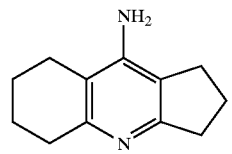

(I)

which comprises the reaction of diphosphorus pentaoxide with a trialkyl phosphate and a hydroxyl compound in a hydrocarbon solvent to thereby prepare a polyphosphoric ester having one or more free hydroxyl groups and serving as a dehydrocondensing agent and using this ester without isolation in the condensation of 2-amino-1-cyclopentene-1-carbonitrile with cyclohexanone through dehydration.

8 Claims, 2 Drawing Sheets

PROCESS FOR THE PREPARATION OF IPIDACRINE OR IPIDACRINE HYDROCHLORIDE HYDRATE

CROSS-REFERENCE TO RELATED APPLICATION

This application claims priority of International Patent Application No. PCT/JP00/04525, filed on Jul. 6, 2000, which in turn claims priority to Japanese Patent Application No. 11-195430, filed on Jul. 9, 1999.

TECHNICAL FIELD

The present invention relates to a process for the preparation of ipidacrine (i.e., 9-amino-2,3,5,6,7,8-hexahydro-lH-cyclopenta [b]quinoline) and ipidacrine hydrochloride hydrate (i.e., 9-amino-2,3,5,6,7,8-hexahydro-lH-cyclopenta [b]quinoline hydrochloride hydrate).

BACKGROUND ART

Ipidacrine hydrochloride hydrate has been reported as a compound having a stimulating effect of transmission at the peripheral nervous system (for example, see JP-B (Kokoku)-63-35611). Further, it has been reported as a compound showing improvement in learning and memory (for example, see JP-B (Kokoku)-3-54922).

As a synthetic process for ipidacrine hydrochloride hydrate, 2-amino-1-cyclopentene-1-carbonitrile (or 1-amino-2-cyanocyclopentene-1) and cyclohexanone are first heated under reflux with polyphosphoric acid in dry benzene to obtain ipidacrine (i.e., 9-amino-2,3,5,6,7,8-hexahydro-lH-cyclopenta[b]quinoline) and hydrogen chloride gas is then passed through the ethanol solution of the resultant reaction mixture to yield ipidacrine hydrochloride hydrate (i.e., 9-amino-2,3,5,6,7,8-hexahydro-1H-cyclopenta [b]quinoline-hydrochloride hydrate) has been reported (for example, see JP-B (Kokoku)-63-35611). Further, it is described that ipidacrine is obtained even if reacting 5,5-pentamethylen-7-oxo-1,2,3,4,6,7-hexahydrocyclopenta [d]pyrimidine obtained as a byproduct in the above reaction with phosphorus oxychloride in toluene (for example, see JP-B (Kokoku)-3-54922).

Further, according to the specification of Japanese Patent No. 2510586, the synthetic method of reaction of 2-amino-1-cyclopentene-1-carbonitrile and cyclohexanone in a solvent such as chloroform in the presence of ethyl polyphosphate at 20 to 100° C. is disclosed.

According to the description in this patent specification, ethyl polyphosphate is prepared by the reaction of diethyl ether and diphosphorus pentaoxide in chloroform.

In order to synthesize ipidacrine hydrochloride hydrate using the method described in the above JP-B-63-35611 or JP-B-3-54922, it is necessary to remove the 5,5-pentamethylene-7-oxo-1,2,3,4,6,7-hexahydrocyclopenta [d]pyrimidine obtained as an impurity during the process, the yield is decreased. Further, the impurity, 5,5-pentamethylene-7-oxo-1,2,3,4,6,7-hexahydrocyclopenta [d]pyrimidine, can be reacted with phosphorus oxychloride according to JP-B (Kokoku)-3-54922 to form ipidacrine hydrochloride hydrate, but such processing is not suitable for mass production, since the number of reaction steps is increased, etc.

Further, the process described in Japanese Patent No. 2510586 is not suitable for industrial-scale mass production, since the procedure for using the highly flammable and hazardous diethyl ether for the preparation of ethyl polyphosphate is extremely complicated and, in addition thereto, a long time (e.g., 3 days) is taken for the preparation. Further, the ethyl polyphosphate prepared has a high viscosity and, therefore, is inconvenient in handling, and also easily changes over time, and therefore, there is the disadvantage that the successive supply of the product having constant quality is extremely difficult. Further, chloroform is used as a reaction solvent, but the use of a large amount of chloroform, which is a type of halomethane, in industrial preparation is a problem in terms of not only work, but also the environment. Therefore, it is hard to say that it is a desirable process.

Further, the ipidacrine generated in the reaction solution after the dehydration condensation reaction in chloroform is separated and purified by a method of addition of water to convert the product to a salt and transfer the same to an aqueous phase, then the aqueous phase is made alkali to precipitate the crystal. However, the chloroform dissolve a considerable amount of the salt of ipidacrine, and therefore, for a increasing of the yield by this method, the chloroform phase should be washed several times (4 times or more). Therefore, this causes the disadvantage of a large number of operation steps.

Further, according to the above three publications, when ipidacrine is hydrochlorated to produce ipidacrine hydrochloride hydrate, ethanol is used as a solvent and hydrogen chloride gas is used as an agent for hydrochlorination. When using an alcoholic solvent such as ethanol as a solvent, a considerable amount of the residual solvent is partially included in the ipidacrine hydrochloride hydrate generated instead of water of crystallization and, therefore, ipidacrine hydrochloride hydrate with insufficient amount of water of crystallization is obtained. The infrared spectrum of this crystal is not idertical with the spectral chart of the standard product and change in the crystal form by X-ray structural analysis, etc. can be observed (for example, see *Iyakuhin Kenkyu* 28, 9, 643–657 (1997)).

Further, since hydrogen chloride gas, which is highly toxic and complicated to handle, is used as an agent for hydrochlorination, the handling cannot be said at all to be easy. Therefore, it is difficult to say that the process is desirable.

DISCLOSURE OF INVENTION

Accordingly, an object of the present invention is to provide a process for the preparation of ipidacrine or ipidacrine hydrochloride hydrate without having the above disadvantages and further in a good yield.

The present inventors engaged in intensive studies to find a process for the preparation of ipidacrine in a good yield, further with little dangerous, easy to carry out, and with little problems in terms of the environment and, as a result, found that these problems were able to be solved by using as a dehydration condensing agent ethyl polyphosphate obtained by reacting diphosphorus pentaoxide with triethyl phosphate and ethanol in a hydrocarbon-based solvent without isolation, conducted further research, whereby the present invention was completed.

Further, we found that in the hydrochlorination step of ipidacrine, by using concentrated hydrochloric acid in an acetone solvent for of hydrochlorination, an ipidacrine hydrochloride hydrate without any change in infrared spectrum or crystal form by X-ray structural analysis is obtained, conducted further research, whereby the present invention was completed.

In accordance with the present invention, there is provided a process for the preparation of ipidacrine (i.e., 9-amino-2,3,5,6,7,8-hexahydro-1H-cyclopenta[b]quinoline) having the formula (I):

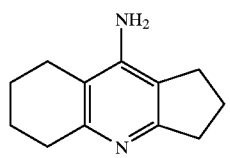

(I)

comprising reacting diphosphorus pentaoxide with trialkyl phosphate and a compound having a hydroxyl group in a hydrocarbon-based solvent so as to prepare a polyphosphate ether partially having a hydroxyl group, as a dehydration condensing agent, then using polyphosphate ester thus obtained, without isolation, for a dehydration condensation reaction of 2-amino-1-cyclopentene-1-carbonitrile and cyclohexanone.

In accordance with the present invention, there is also provided a process for the preparation of ipidacrine hydrochloride hydrate comprising of the reaction of ipidacrine with concentrated hydrochloric acid in acetone or in a mixed solvent of acetone with a small amount of water for hydrochlorination.

In accordance with the present invention, there is further provided a process for the preparation of ipidacrine hydrochloride hydrate, wherein the ipidacrine hydrochloride hydrate shows an infrared absorption spectrum of a standard product without containing residual solvent (Type A).

BRIEF DESCRIPTION OF DRAWINGS

The present invention will be explained below with reference to the following drawings, wherein.

BEST MODE FOR CARRYING OUT THE INVENTION

Figure 1:
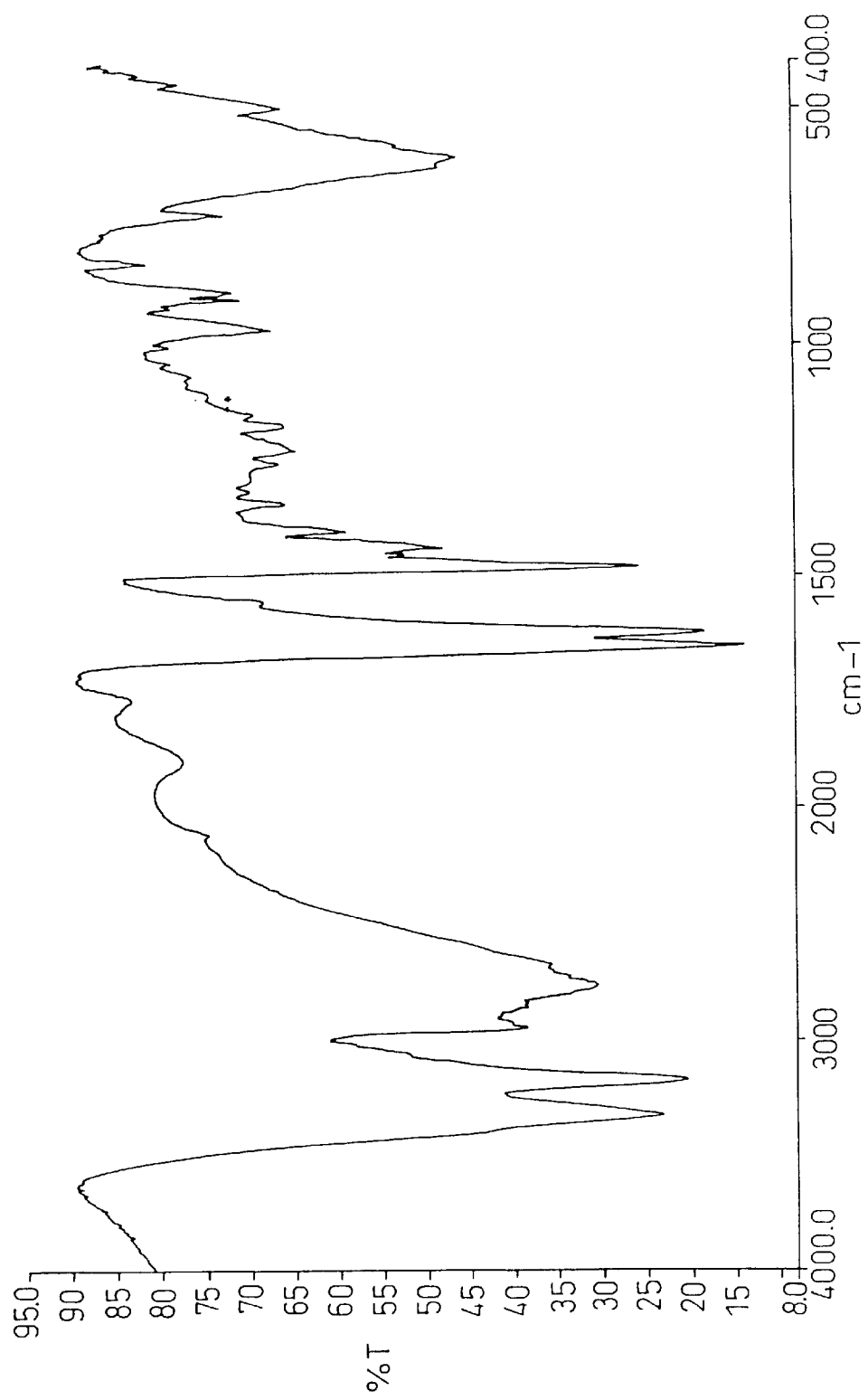
FIG. 1 is a view of a Type A infrared spectrum of ipidacrine hydrochloride hydrate.
Figure 2:
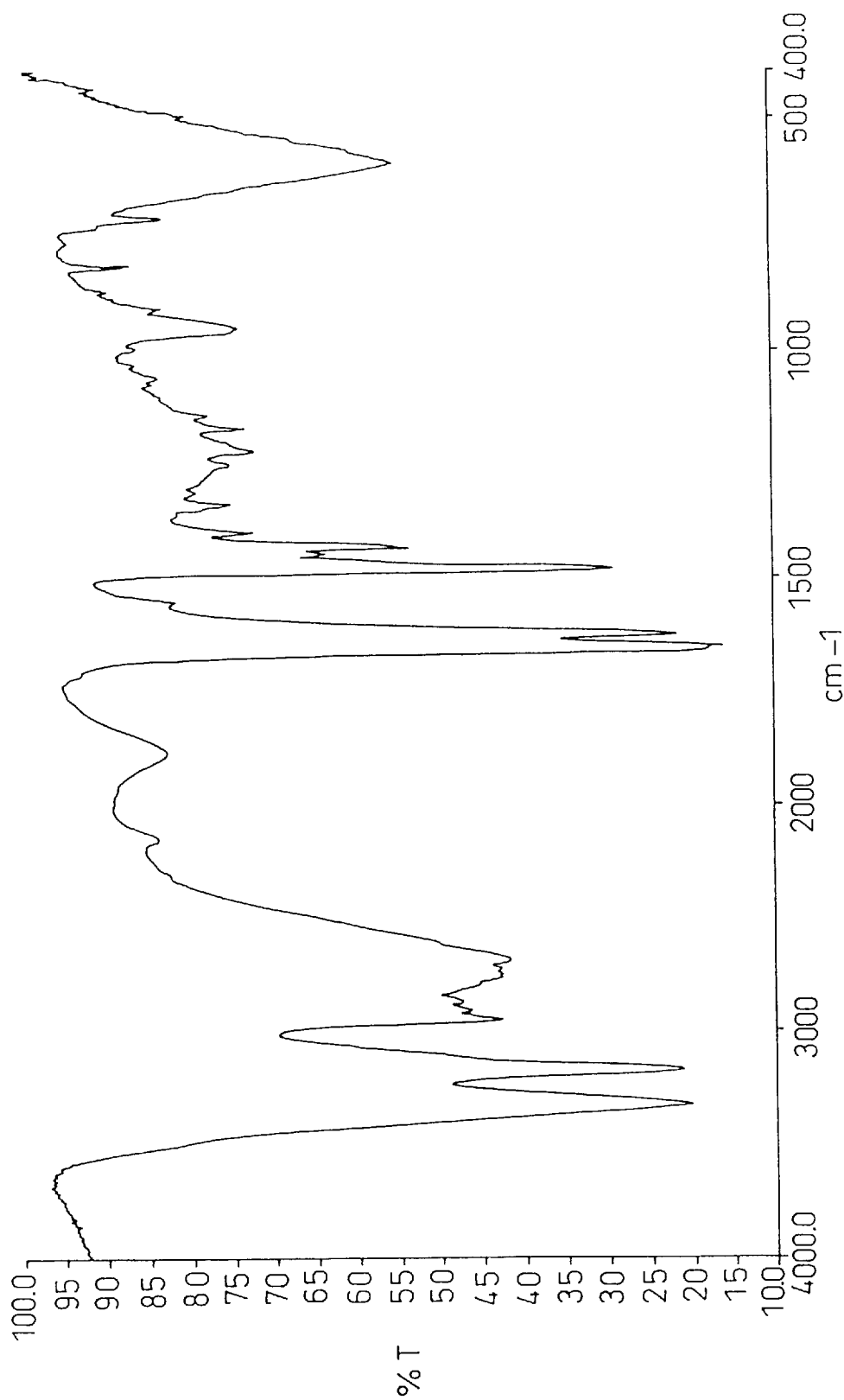
FIG. 2 is a view of a Type B infrared spectrum of ipidacrine hydrochloride hydrate.

The present invention will be explained in further detail below.

The ipidacrine (i.e., 9-amino-2,3,5,6,7,8-hexahydro-1H-cyclopenta [b]quinoline) used in the present invention usually means an anhydride, but in the present specification, is considered to include also an ipidacrine hydrate (theoretical amount of hydrate) or one with an amount of moisture not more than monohydrate. This is because, if ipidacrine (anhydride, amorphous crystal) is allowed to stand in the air at room temperature, it naturally absorbs the moisture in the air and becomes a stable monohydrate. Further, for example, if ipidacrine is recrystallized in a methanol-water mixed solvent or a hydrous organic solvent such as an acetone-water mixed solvent, ipidacrine monohydrate (needle crystals etc.) is obtained. The ipidacrine monohydrate or crystals of the hydrate including water of a theosetical amount for the monohydrate or less normally easily lose their water of crystallization and become anhydrides when heated and dried in vacuo.

The polyphosphate ester partially having a hydroxyl group used in the present invention is characterized by part of its structure having a P—OH residual group. A polyphosphate ester obtained by a reaction of diphosphorus pentaoxide and a theoretical amount of trialkyl phosphate is a polymer not having a P—OH residual group in the structure thereof. However when this polyphosphate ester is used as a condensing agent, a byproduct is generated or the starting material is decomposed during the reaction. Not only the yield of the ipidacrine is decreased, but also a colored ipidacrine having a low purity is obtained.

In the present invention, a polyphosphate ester having a P—OH residual group in the part of its structure is used, byproducts are not produced and the starting material is not decomposed as above, and, therefore, a high purity ipidacrine is obtained in a high yield.

The polyphosphate ester partially having a hydroxyl group used in the present invention can be prepared by the following process. That is, the diphosphorus pentaoxide is suspended in an organic solvent unreacted with diphosphorus pentaoxide, for example, a hydrocarbon-based organic solvent such as toluene, benzene and trialkyl phosphate added dropwise while heating to a suitable temperature. The reaction proceeds quickly, and therefore, so the compound having a hydroxyl group (i.e., the compound having -OH residual group in molecule), for example, ethanol, water, etc., is added immediately after the dropwise addition or shortly after it. The reaction normally is exothermie, and therefore, if necessary, the solution is cooled to a suitable temperature. This reaction also proceeds quickly, and therefore, the preparation of the polyphosphate ester is finished the point of time, when the dropwise addition is completed.

As the trialkyl phosphate used in the present invention, triethyl phosphate, trimethyl phosphate, etc. may be mentioned. In the present invention, in most cases, triethyl phosphate is used.

Examples of the compound having a hydroxyl group are an alcohol, water, polyphosphoric acid, pyrophosphoric acid, phosphoric acid. Preferably compound is an alcohol. These compounds may be used alone or in any mixtures thereof.

As the alcohol, a monovalent alcohol such as methanol, ethanol, or propanol is preferable. In addition, a polyhydric alcohol such as ethylene glycol or glycerol may also be used.

The hydrocarbon-based solvent may be a solvent not reacting with diphosphorus pentaoxide. Specifically, benzene, toluene, xylene, etc. or mixtures thereof may be exemplified, but toluene is preferable from the viewpoint of toxicity and cost.

The diphosphorus pentaoxide is usually used in an amount of 3 to 10 equivalents by molar ratio based upon the 2-amino-1-cyclopentane-1-carbonitrile, but 3 to 8 equivalents by molar ratio is preferably used from the viewpoint of the reaction yield and cost.

The trialkyl phosphate is usually used in an amount of 0.3 to 1.2 equivalents by molar ratio based upon the diphosphorus pentaoxide, but 0.4 to 1 equivalent by molar ratio is preferably used from the viewpoint of the reaction yield, operating procedure, and cost.

When an alcohol is used as the compound having a hydroxyl group, the alcohol is usually used in an amount of 0.05 to 1 equivalent by molar ratio based upon the diphosphorus pentaoxide, preferably 0.1 to 0.6 equivalent.

Further, instead of the alcohol, it is possible to use water, polyphosphoric acid, pyrophosphoric acid, or phosphoric acid, but in this case, molar quantity is adjusted so that the number of P—OH groups of the polyphosphate ester obtained becomes to be equal in the case of use of an alcohol such as ethanol. That is, in the case of water, ½ an equivalent based upon the alcohol is preferable, while in the case of phosphoric acid, ⅓ an equivalent is preferable.

In the reaction process for of reacting diphosphorus pentaoxide with trialkyl phosphate and alcohol (or a compound having an —OH group in the molecule) in a hydrocarbon-based solvent, the reaction can normally be performed at a temperature of 0° C. to 100° C., preferably 30° C. to 80° C. The reaction is normally completed within 6 hours.

In the dehydration condensation reaction step of the 2-amino-1-cyclopentene-1-carbonitrile and cyclohexanone, the reaction can normally be carried out at a temperature of 0° C. to 110° C., preferably 30° C. to 80° C. The reaction is normally completed from 1 to 6 hours.

After the end of the reaction, to separate and purify the product from the reaction solution, it is possible to easily obtain a purified product by suitably selecting a method such as solvent extraction, crystallization, activated carbon treatment, column chromatography, etc., or in some cases using a combination of the same.

In the past, when preparing a polyphosphoric acid or polyphosphate ester-based dehydrating agent from diphosphorus pentaoxide, there was the disadvantage that the stirring became extremely difficult since a viscous substance was appeared during the dropwise addition when using a compound easily reactable with diphosphorus pentaoxide such as water, alcohol, etc. On the other hand, with a compound hard to react with diphosphorus pentaoxide such as diethyl ether, a viscous substance is not easily appeared, but conversely there is the disadvantage that the preparation time becomes extremely long.

According to the present invention, in the step of preparation of the polyphosphate ester, trialkyl phosphate and alcohol (or a compound having an -OH residual group in its molecule) are reacted with the diphosphorus pentaoxide. Further, a hydrocarbon-based solvent is used as the solvent in this step. Toluene is used as a particularly preferable solvent. The reaction of the diphosphorus pentaoxide used in the preparation of the polyphosphate ester, trialkyl phosphate and alcohol (or compound having an —OH residual group in its molecule) is an exothermic reaction, but the reaction proceeds under moderate conditions, and therefore, is suitable for industrial production. Further, this reaction completes within a short time, in most cases, within one hour, and therefore, is advantageous in regard to the manufacturing costs as well.

In the present invention, the polyphosphate ester synthesized has the advantage of being usable for the dehydration condensation reaction of 2-amino-1-cyclopentene-1-carbonitrile and cyclohexanone as it is, without isolation. Therefore, it is possible to avoid deterioration of the quality of the polyphosphate ester along with time. Further, a polyphosphate ester is decomposed by the addition of water and ipidacrine is transferred to the aqueous phase as the ipidacrine phosphate. At that time, the salt of synthesized ipidacrine does not dissolve much at all in a hydrocarbon-based solvent such as toluene, and therefore, there is the advantage that the separation and purification of the product are easy.

It is possible to obtain ipidacrine by addition of an aqueous solution of sodium hydroxide to the ipidacrine phosphate transferred to the aqueous phase in this way and obtaining the precipitated crystal by filtration. It is possible to easily obtain purified ipidacrine from the precipitated crystal by suitably selecting a method such as solvent extraction, crystallization, column chromatography, etc. and in some cases using a combination of the same. In the present invention, normally it is possible to obtain ipidacrine purified by recrystallization in a mixed solvent of methanol and water.

In the process of hydrochlorination of the ipidacrine of the present invention, if causing a reaction with concentrated hydrochloric acid in a solvent such as acetone or a mixed solvent of acetone with a small amount of water, ipidacrine hydrochloride hydrate not exhibiting any difference in infrared spectrum or crystal form by X-ray structural analysis is obtained. In this case, even if using complete anhydrous ipidacrine and using only acetone as a solvent, due to the effect of the water contained in the hydrochloric acid, a monohydrate monohydrochloride, that is, ipidacrine hydrochloride hydrate, is obtained.

The amount of water in the mixed solvent of acetone with a small amount of water is normally not more than $\frac{1}{5}$, preferably not more than $\frac{1}{10}$, by volume ratio, based upon the acetone. If the amount of water in the mixed solvent becomes large, the ipidacrine hydrochloride hydrate easily dissolves in water, and therefore this decreases a yield and, therefore, is not desirable.

If the hydrochloride is filtered and dried, the excess acetone is removed from the hydrochloride obtained, an ipidacrine hydrochloride hydrate with the theoretical amount, that is, one molecule, of water of crystallization attached is obtained. The infrared spectrum of the crystal is consistent with the standard spectrum. The crystal form by X-ray structural analysis also is the same as that of a standard product.

Further, sometimes a small amount (normally not more than 300 ppm) of acetone remains in the ipidacrine hydrochloride hydrate obtained in the present invention, but in this case, the acetone can be easily completely removed by allowing the crystal to stand in a high temperature, high humidity atmosphere or adding a small amount of water to the crystal, then mixing and drying.

EXAMPLES

The present invention will now be further explained in more detail by, but is by no means limited to, the following Examples.

Example 1

Synthesis of 9-amino-2,3,5.6,7.8-hexahvdro-1H-cyclopentafbiquinoline)

78.8 g (555 mmol) of diphosphorus pentaoxide ($P_2O_5$) was suspended in 100 ml of toluene and raised in temperature to 55° C. At that temperature, 78.6 ml (462 mmol) of triethyl phosphate was added dropwise, then 8.0 ml (139 mmol) of ethanol was added dropwise and stirred for 30 minutes. The solution was cooled to 20° C., 10.0 g (92.5 mmol) of 2-amino-1-cyclopentene-1-carbonitrile and 10.1 ml (97.1 mmol) of cyclohexanone were added, then the solution was stirred at 55° C. for 3.5 hours. The solution was cooled, then 200 ml of water was added dropwise at not more than 40° C. and stirred at 55° C. for 30 minutes. The aqueous phase was separated and the toluene phase was washed with 100 ml of water. The resultant aqueous phase was combined with the previously separated aqueous phase.

The aqueous phase was added dropwise into 400 ml of a concentrated ammonia water solution and the resultant mixture was extracted with a mixed solution of chloroform-methanol (10:1). The extract was dried over anhydrous magnesium sulfate, then the solvent was evaporated in vacuo. The residue was purified by silica gel chromatography (silica gel 300 g; chloroform:methanol:concentrated ammonia water=100:9:1), then dried in vacuo at 60° C., to obtain 15.8 g of the desired compound (90.7% yield).

¹H-NMR (400 MHz, CDCl3):1.80–1.91 (4H, m), 2.11 (2H, dd, J=7.3, 7.6 Hz), 2.40–2.46 (2H, m), 2.70 (2H, t, J=7.3 Hz), 2.80–2.86 (2H, m), 2.92 (2H, t, J=7.6 Hz), 3.91 (2H, br)

Example 2

Synthesis of Ipidacrine (i.e. 9-Amino-2,3,5,6,7,8-hexahydro-1H-cyclopenta[b]quinoline)

394 g (2774 mmol) of diphosphorus pentaoxide ($P_2O0$) was suspended in 500 ml of toluene and raised in temperature to 55° C. At that temperature, 283 ml (1665 mmol) of triethyl phosphate was added dropwise, then 75 ml (1295 mmol) of ethanol was added dropwise and the resultant mixture was stirred for 30 minutes. The solution was cooled to 30° C., 50 g (462 mmol) of 2-amino-1-cyclopentene-1-carbonitrile and 50 ml (485 mmol) of cyclohexanone were added, then the solution was stirred at 55° C. for 3.5 hours. The heating was stopped, 500 ml of water was added dropwise at not more than 55° C., and the solution was stirred at 55° C. for 30 minutes. The aqueous phase was separated and the toluene phase was washed by 250 ml of water. The resultant aqueous phase was combined with the previously separated aqueous phase.

The aqueous phase was added dropwise into 2000 ml of an 18% sodium hydroxide aqueous solution, then the precipitated crystal was collected by filtration and rinsed well. The hydrous crystal obtained was dissolved by heating to a mixed solvent of 750 ml of methanol and 1500 ml of water and the resultant solution was cooled for recrystallization. The precipitated crystal was filtered, rinsed, then dried in vacuo at 60° C. to obtain 79 g (420 mmol) of the desired compound as an anhydride. The yield was 91%.

Example 3

Synthesis of Ipidacrine Hydrochloride Hydrate (9-amino-2,3,5,6,7,8-hexahydro-1H-cyclolpenta[b]quinoline-hydrochloride Hydrate 40 g (212 mmol) of ipidacrine (i.e., 9-amino-2,3,5,6,7,8-hexahydro-1H-cyclopenta[b]quinoline) was heated and dissolved in a mixed solvent of 720 ml of acetone and 40 ml of water. 19 ml (212 mmol) of concentrated hydrochloric acid was added dropwise over 10 minutes. Further, the solution was heated under reflux for 30 minutes, then allowed to stand at room temperature overnight. The precipitated crystal was filtered, washed with acetone, then allowed to stand in the air to allow the deposited acetone to evaporate, and obtained 49 g (202 mmol) of the desired compound. The yield was 95%. The melting point was 274° C. (decomposition).

Example 4

Ipidacrine hydrochloride hydrate was produced under substantially the same conditions as in Example 2 other than the amounts of the ipidacrine, acetone, and water. The yield, moisture content, and infrared spectrum of the ipidacrine hydrochloride hydrate thus obtained are shown in Table I.

TABLE I

| Ipidacrine (g) | Acetone (ml) | Water (ml) | Yield (%) | Moisture content (%) | IR |
|---|---|---|---|---|---|
| 10 | 200 | 0 | 98 | 7.40 | Type A |
| 10 | 140 | 10 | 89 | 7.40 | Type A |

TABLE I-continued

| Ipidacrine (g) | Acetone (ml) | Water (ml) | Yield (%) | Moisture content (%) | IR |
|---|---|---|---|---|---|
| 200 | 3000 | 200 | 95 | 7.45 | Type A |
| 10 | 180 | 10 | 92 | — | Type A |
| 200 | 3600 | 200 | 95 | 7.51 | Type A |
| 600 | 8500 | 600 | 94 | 7.35 | Type A |
| 300 | 4100 | 300 | 95 | 7.33 | Type A |

(Note) "—" marks in moisture content column indicate not yet measured.

Type A of the IR spectrum indicates identification with the infrared spectrum of a standard product.

Reference Example 1

A partial hydrate of ipidacrine hydrochloride was recrystallized from 2-propanol, the solvent was distilled off, then the residue was dried at 60° C. in vacuo for 3 days to obtain a recrystallized product (moisture content: 3.01%). Next, 15 g of the recrystallized product was allowed to stand under moist conditions (40° C., 75%) for 2 days to obtain ipidacrine hydrochloride hydrate.

The infrared spectrum of the compound is not consistent with the infrared spectrum of the standard product and exhibits the infrared spectrum of Type B of the residual solvent.

INDUSTRIAL APPLICABILITY

The present invention can use a polyphosphate ester obtained by the reaction of diphosphorus pentaoxide with trialkyl phosphate and an alcohol or another compound having a hydroxyl group in a hydrocarbon-based solvent, preferably tolune, as a condensing agent for synthesis of ipidacrine as it is without isolation and can obtain ipidacrine by a condensation reaction in an extremely high yield. Therefore, the present invention is an extremely preferable process from the viewpoints of the improvement of the yield, of course, and hazard, work efficiency, and the environment compared with the use of polyphosphate ester prepared in advance.

Further, ipidacrine can easily be converted into ipidacrine hydrochloride hydride by using of concentrated hydrochloric acid in acetone or in a mixed solvent of acetone and a small amount of water. Further, the crystal exhibits the infrared spectrum (Type A) of the standard product not including residual solvent, and therefore, has the advantage of being able to be used as a pharmaceutical ingredient as it is.

What is claimed is:

1. A process for the preparation of ipidacrine (i.e., 9-amino-2,3,5,6,7,8-hexahydro-1H-cyclopenta[b]quinoline) having the formula (I):

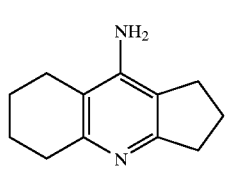

(I)

comprising the reaction of diphosphorus pentaoxide with trialkyl phosphate and a compound having a hydroxyl group in a hydrocarbon-based solvent so as to produce a polyphosphate ester partially having a hydroxyl group as a dehydration condensing agent, then using the thus obtained polyphosphate: ester without isolation for a dehydration condensation reaction of 2-amino-i-cyclopentene-1-carbonitrile and cyclohexanone.

2. A process for the preparation of ipidacrine as claimed in claim 1, wherein the hydrocarbon-based solvent is benzene, tolune, or xylene.

3. A process for the preparation of ipidacrine as claimed in claim 1, wherein the trialkyl phosphate is triethyl phosphate orztrimethyl phosphate.

4. A process for the preparation of ipidacrine as claimed in claim 1, herein the compound having a hydroxyl group is alcohol, water, polyphosphoric acid, pyrophosphoric acid, or phosphoric acid.

5. A process for the preparation of ipidacrine as claimed in claim 1, wherein the compound having a hydroxyl group is an alcohol selected from methanol, ethanol, or propanol.

6. A process for the preparation of ipidacrine as claimed in claim 1, comprising reacting diphosphorus pentaoxide with triethyl phosphate and ethanol in toluene to produce ethyl polyphosphate partially having a hydroxyl group.

7. A process for the preparation of ipidacrine hydrochloride hydrate (9-amino-2,3,5,6,7,8-hexahydro-1H-cyclopenta[b]quinoline-hydrochloride-hydrate) comprising reacting ipidacrine obtained from any one of claims 1 to 6 with concentrated hydrochloric acid in acetone or in a mixed solvent comprised of acetone and a small amount of water for hydrochloration.

8. A process for the preparation of ipidacrine hydrochloride hydrate as claimed in claim 7, wherein the ipidacrine hydrochloride hydrate shows an infrared absorption spectrum of a standard product not containing residual solvent (Type A).

* * * * *